United States Patent [19]

Meir

[11] Patent Number: 4,696,182
[45] Date of Patent: Sep. 29, 1987

[54] IMPACT TEST APPARATUS

[75] Inventor: Avraham A. Meir, Willow Grove, Pa.

[73] Assignee: Seti Inc., Montgomeryville, Pa.

[21] Appl. No.: 872,720

[22] Filed: Jun. 10, 1986

[51] Int. Cl.$^4$ .............................................. G01N 3/30
[52] U.S. Cl. ........................................... 73/12; 73/167
[58] Field of Search ..................................... 73/12, 167

[56] References Cited

U.S. PATENT DOCUMENTS

| | | | |
|---|---|---|---|
| 2,537,096 | 1/1951 | Shreeve, Jr. et al. | 73/12 |
| 2,604,777 | 7/1952 | Armstrong et al. | 73/12 |
| 3,693,432 | 9/1972 | Stewart et al. | 73/167 |

Primary Examiner—Charles A. Ruehl
Attorney, Agent, or Firm—Panitch Schwarze Jacobs and Nadel

[57] ABSTRACT

An impact test apparatus includes a barrel adapted to contain pressurized gas and having a sealed end and an opposed open end. A shuttle including a bore for carrying a test sample is positioned for translation within the barrel. A seal is provided on the shuttle for sealingly engaging the barrel. The seal divides the interior of the barrel into a portion open to the atmosphere and a sealed portion. A trigger element selectively retains the shuttle in a fixed position within the barrel and permits the shuttle to be released to accelerate toward the open of the barrel as the pressurized gas in the sealed portion of the barrel expands. Brake rings are located proximate the open end of the barrel to decelerate the shuttle and retain the shuttle substantially within the barrel while allowing the test sample to travel towards a target aligned with the open end of the barrel. The impact test apparatus permits reliable and reproducible impact testing of projectiles without the use of towers or explosive charges.

16 Claims, 7 Drawing Figures

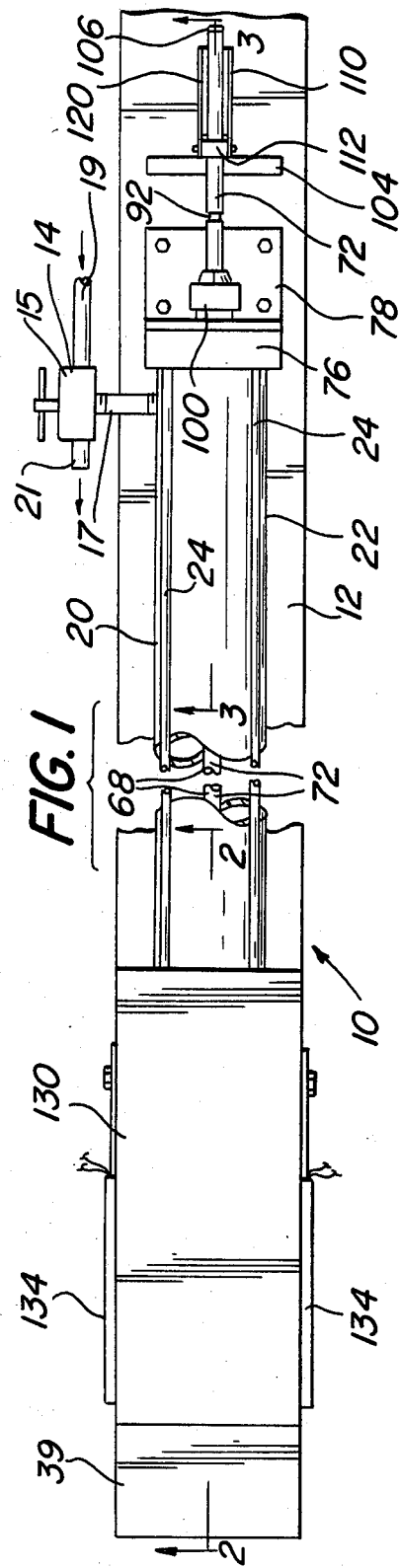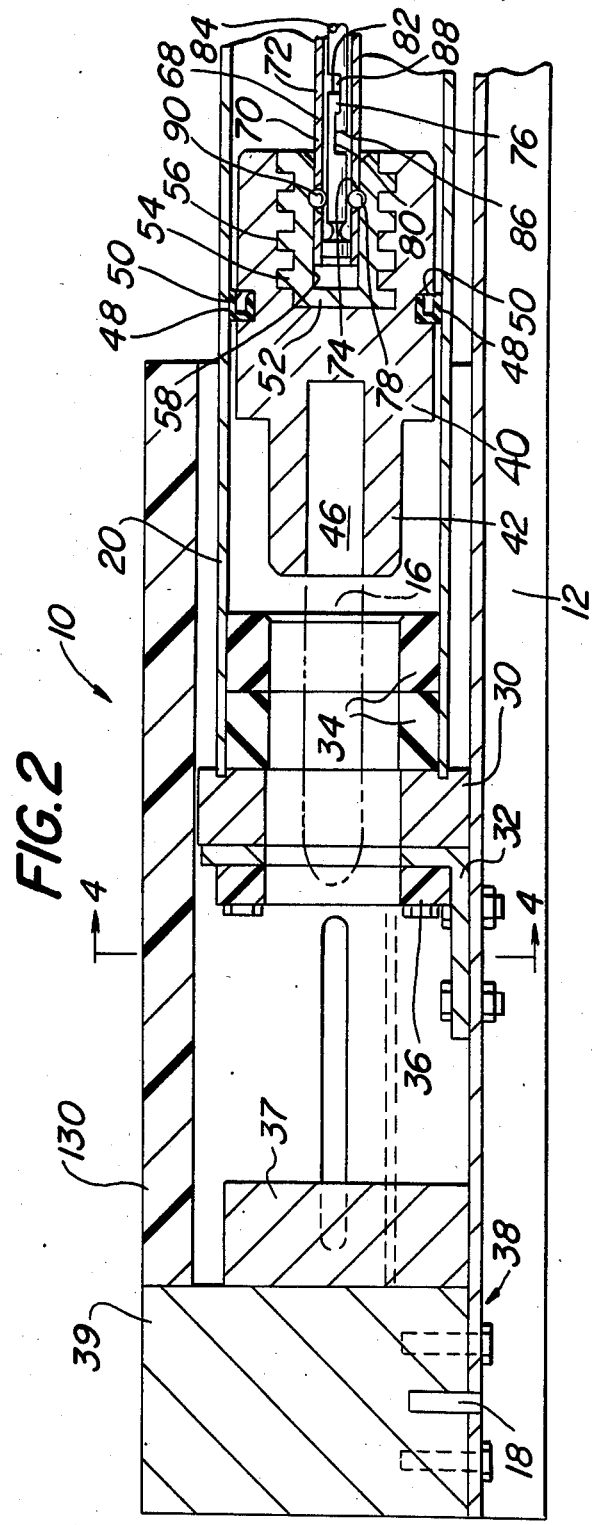

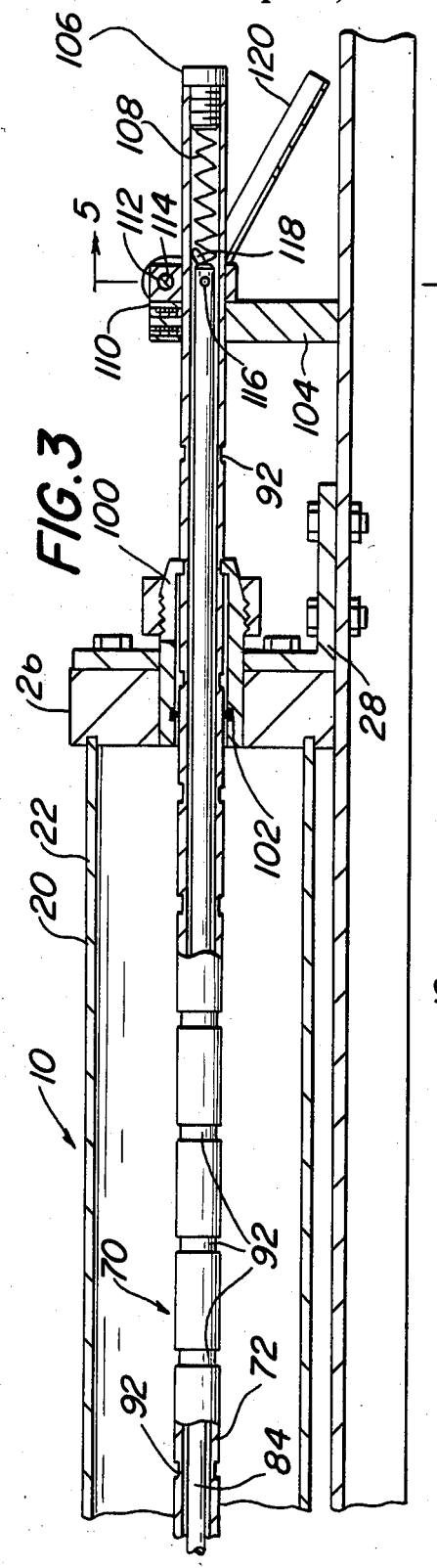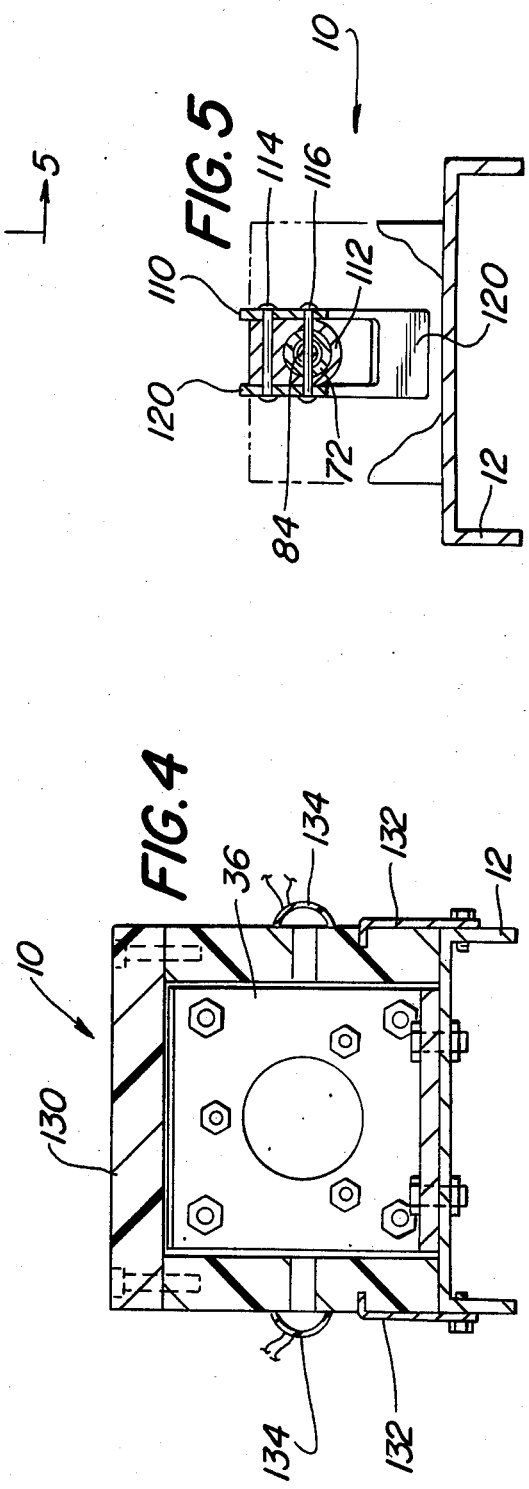

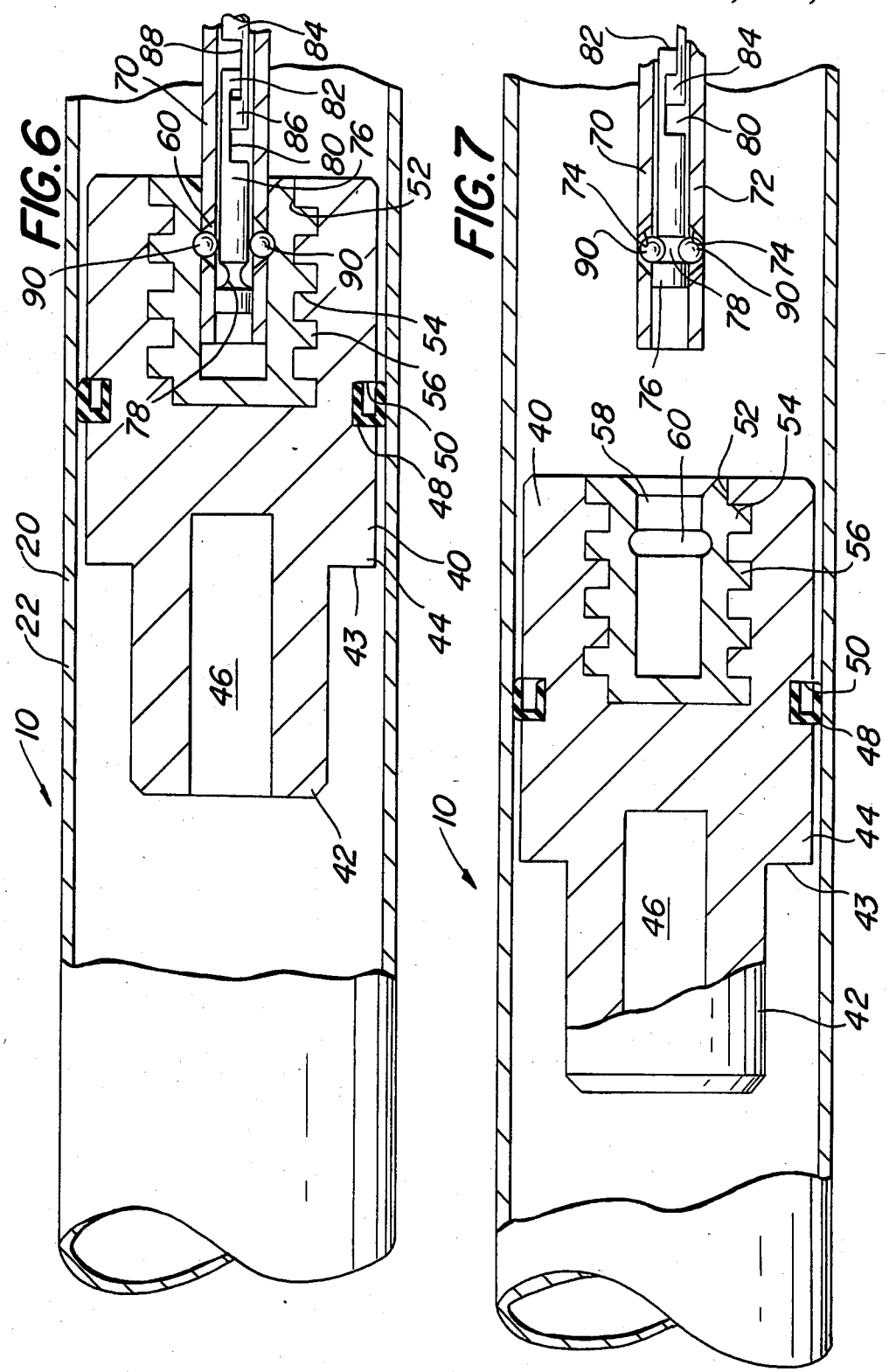

IMPACT TEST APPARATUS

BACKGROUND OF THE INVENTION

The present invention relates generally to an impact test apparatus, and more particularly to an apparatus for reliably and reproducibly launching samples for impact testing without the use of high towers for gravitationally accelerating the test samples, explosive charges, or the like.

The testing of projectiles and their components is an important aspect of military preparedness. While many aspects of the performance and characteristics of projectiles can be modeled mathematically using sophisticated computer techniques, modeling can do no more than predict actual performance. On the other hand, performance under actual service conditions is often difficult to assess because there are a number of uncontrollable variables including atmospheric conditions, such as temperature, humidity, and the like, encountered during the test. Further, field testing of projectiles is often difficult and expensive. It is desirable to be able to simulate the actual conditions encountered by a projectile in the field by laboratory testing. A laboratory test should provide a means of controlling and monitoring important variables like the muzzle velocity of the projectile.

One important aspect of the testing of projectiles and their components is impact testing. Impact tests are often carried out by dropping test samples from high towers, a practice requiring a significant amount of dedicated laboratory space and capital expenditure. Further, because the test sample must travel a significant distance while it is being accelerated by gravity, any imbalance in the aerodynamic resistance encountered while falling will cause the test sample to rotate from its initial orientation, making its orientation on impact unpredictable and uncontrollable. Impact testing is also important in the evaluation of many types of industrial and consumer products.

The present invention provides impact test apparatus for reliably and reproducibly launching a projectile, projectile component, or other test sample for impact testing. Further, the present invention provides a number of other advantages and capabilities as are discussed below.

SUMMARY OF THE INVENTION

The present invention provides an impact test apparatus including a barrel adapted to contain pressurized gas and having a sealed end and an opposed open end. The test apparatus further includes a shuttle positioned for translation within the barrel. The shuttle includes means for carrying a test sample and sealing means for sealingly engaging the barrel. The sealing means divides the interior of the barrel into a portion open to the atmosphere and a sealed portion.

Means are provided for supplying pressurized gas to the sealed portion of the interior of the barrel. In addition, the test apparatus includes trigger means for selectively retaining the shuttle in a fixed position in the barrel and for releasing the shuttle to permit the shuttle to accelerate toward the open end of the barrel as the pressurized gas in the sealed portion of the barrel expands. Stopping means are provided proximate the open end of the barrel to decelerate the shuttle and retain the shuttle substantially within the barrel while allowing the test sample to travel toward a target aligned with the open end of the barrel.

Preferably, the stopping means includes at least one brake ring formed from a resilient material and having an exterior surface shaped to abut the interior of the barrel. An axially centered opening in the brake ring is adapted to engage the shuttle. A ring retention means is provided for retaining the brake ring in the barrel when the brake ring is engaged by the shuttle.

BRIEF DESCRIPTION OF THE DRAWINGS

FIG. 1 is a broken plan view of an impact test apparatus according to a presently preferred embodiment of the present invention;

FIG. 2 is a partial vertical sectional view taken along the line 2—2 of FIG. 1;

FIG. 3 is a partial vertical sectional view taken along the line 3—3 of FIG. 1;

FIG. 4 is a vertical sectional view taken along the line 4—4 of FIG. 2;

FIG. 5 is a partially broken vertical sectional view taken along the line 5—5 of FIG. 3;

FIG. 6 is an enlarged, partially broken, vertical partially sectional view of the impact test apparatus of FIG. 1 showing the shuttle engaged by the trigger means; and FIG. 7 is an enlarged, partially broken, vertical partially sectional view of the impact test apparatus of FIG. 6 showing the shuttle disengaged and released from the trigger means.

DETAILED DESCRIPTION OF THE PREFERRED EMBODIMENT

Referring in detail to the drawings, wherein like numerals indicate like elements throughout the several figures, there is shown in FIG. 1 a broken plan view of an impact test apparatus 10 in accordance with a presently preferred embodiment of the present invention. The impact test apparatus 10 includes a generally cylindrical barrel 20 mounted on a base 12 and sealed at one end by a first or rear end member 26. As used in the present specification, "front" refers to the direction of the end of the barrel 20 from which the test sample emerges and "rear" refers to the opposite direction.

As best seen in the vertical sectional view of FIG. 2, which illustrates the front end of the impact apparatus 10, the barrel 20 contains a shuttle 40 positioned for translation within the barrel 20 and having a generally cylindrical, axial sample chamber or front bore 46 adapted to contain a test sample or projectile 16. The barrel 20 is open at the second or front end of the barrel 20. The shuttle 40 is retained selectively in a fixed position in the barrel by a releasable trigger means 68.

As discussed in detail below, in operation a projectile 16 is placed in the shuttle 40 and the barrel 20 is filled with compressed gas through a gas supply means 14 (FIG. 1). The trigger means 68 is actuated by an operator, thereby releasing the shuttle 40 from the trigger means 68 and permitting the shuttle 40 to accelerate toward the open end of the barrel 20 as the compressed gas within the barrel 20 expands. A plurality of stop rings 34 (FIG. 2) and a front end member 30 are provided to retain the shuttle 40 substantially within the barrel 20. However, the projectile 16 is free to continue in a trajectory from the shuttle 40 to a target 38 aligned with the open end of the barrel 20. The projectile 16 impacts against the target 38 and the results of the impact on the projectile 16 can be studied subsequently.

The barrel 20 includes a generally cylindrical tube 22 preferably formed from a rigid material having high structural strength, for example, brass, steel, and the like, which can safely contain compressed gas at elevated pressures. As illustrated in FIGS. 2 and 3, the ends of the tube 22 are contained within generally annular circular grooves formed in the front end member 30 and the rear end member 26. A gas-tight seal is made between the tube 22 and the rear end member 26. If necessary to achieve the gas-tight seal, a gasket (not illustrated) such as an O-ring formed from a compressible elastomer can be inserted into the generally circular groove in the rear end member 26 before the end of the tube 22 is placed in the groove. The front and rear end members 30, 26 are securely affixed to the ends of the tube 22 by a plurality of tie rods 24 (best seen in FIG. 1) extending between and affixed to the rear end member 26 and front end member 30 outside the tube 22. The tie rods 24 aid in securely maintaining the end members 26, 30 in place on the tube 22 when the impact test apparatus 10 is in use. Both the front end member 30 and rear end member 26 are secured to the base 12 by generally "L"-shaped brackets 32, 28, respectively, by threaded fastening members such as bolts. As seen in FIGS. 1, 2 and 3, both the front end member 30 and the rear end member 26 have generally rectangular cross sections and generally cylindrical axial apertures as discussed further below.

As best seen in the enlarged partially broken vertical sectional view of FIG. 7, the shuttle 40 includes a generally cylindrical front section 42 having a generally circular face and an exterior diameter somewhat smaller than the interior diameter of the tube 22. The edge formed between the front face and the exterior cylindrical surface of the front section 42 of the shuttle 40 is chamfered. Formed integrally and coaxially with the front section 42 is a generally cylindrical rear section 44 having an exterior diameter slightly less than the interior diameter of the tube 22. A generally annular shoulder 43 is formed between the front section 42 and the rear section 44 of the shuttle 40. A generally annular circular groove 50 is provided in the exterior surface of the rear section 44 and contains a generally annular ring-shaped sealing means or seal 48 formed from a resilient material such as a natural or synthetic elastomer and adapted to sealingly but slidingly engage the interior surface of the tube 22. The seal 48 divides the interior of the barrel 20 into a portion open to the atmosphere extending forward from the seal 48 to the front end of the barrel 20 and a sealed portion extending rearward from the seal 48 to the rear end of the barrel 20. If desired, multiple seals can be provided. The shuttle 40 is preferably formed of a light weight, high strength material such as aluminum, or durable synthetic polymeric material, such as nylon.

While the sample chamber 46 has a generally cylindrical shape, other geometries can be used depending on the characteristics of the projectile 16 or other sample to be tested in the impact test apparatus 10. For example, the interior of the sample chamber 46 can be provided with protrusions to aid in aligning the sample, if desired (not illustrated). Similarly, the cross section of the sample chamber 46 can be adapted to reflect the exterior geometry of the sample. For example, when a sample having a rectangular cross section is to be tested, the sample chamber 46 can itself have a rectangular cross section of slightly greater dimension than the sample (not illustrated). However, it is preferred that the sample chamber 46 be axially centered in the face of the front section 42 of the shuttle 40, whatever geometry is adopted for the sample chamber 46.

As shown in FIG. 1, the compressed gas supply means 14 includes valve means 15 for placing the interior of the barrel 20 in fluid communication via conduits 17 and 19 with a source of gas under pressure (not shown), such as a cylinder of compressed gas or a gas compressor. The valve means 15 also places the interior of the barrel 20 in fluid communication with the atmosphere via conduits 17 and 21, thereby permitting gas contained within the barrel 20 under elevated pressure to be exhausted therefrom. Preferably, the compressed gas supply 14 includes regulator means for precisely regulating the pressure of the gas supplied to the barrel 20. Because both the pressure of the gas within the barrel 20 and, as described in detail below, the position of the shuttle 40 can be precisely and reproducibly controlled, the conditions of a test performed with the impact test apparatus 10 of the present invention are reproducible.

Any type of compressed gas can be used to power the impact test apparatus 10. While compressed air is satisfactory, other types of compressed gases such as nitrogen and argon may also be employed. The muzzle velocity of the impact test apparatus 10 can be varied by adjusting the pressure of the compressed gas contained within the barrel 10.

When the shuttle 40 is released as described below, expansion of compressed gas in the sealed portion of the barrel 20 accelerates the shuttle 40 carrying a projectile 16 (FIG. 2) forward. Positioned within the tube 22 adjacent the front end member 30 are a plurality of generally ring-shaped brake members 34 formed from a resilient material such as a synthetic or natural elastomer. Each of the brake members 34 has a generally cylindrical exterior surface which abuts the interior of the tube 22 and a generally cylindrical axial aperture. The diameter of the axial apertures of the brake members 34 is slightly less than the exterior diameter of the front section 42 of the shuttle 40. The brake rings 34 are retained inside the barrel 20 by ring retention means in the form of the front end member 30, the bracket 32, and a front plate 36, as best seen in FIGS. 2 and 4.

When the shuttle 40 propelled within the barrel 20 by the force of the expanding compressed gas encounters the brake rings 34, the front section 42 of the shuttle is centered by the chamfer on the end of the front section 42 within the axial aperture of the brake ring 34 which the shuttle 40 first encounters. Because the exterior diameter of the front section 42 of the shuttle 40 is greater than the interior diameter of the brake ring 34, the brake ring 34 is compressed between the front section 42 and the tube 22. A generally ring-shaped, sealed volume of air is thus formed between the brake ring 34 and the seal 48 of the shuttle 40. The forward motion of the shuttle 40 is retarded both by the frictional force exerted by the brake ring 34 against the front section 42 of the shuttle and by the force opposing compression of the gas trapped between the brake ring 34 and the seal 48. Ultimately, this combination of forces causes the shuttle 40 to come to rest.

While the shuttle 40 is retained within the barrel 20, the projectile 16 leaves the barrel 20 through the apertures formed in the brake rings 34, the front end member 30, the bracket 32 and the front plate 36. The projectile 16 continues in its trajectory until it impacts on a target 38. The target 38 includes a target support 39 formed from a massive block of high strength material, such as steel. The target support 39 is precisely and reproducibly positioned on the base 12 by pins 18 and is secured to the base 12 by threaded fastener means such as bolts. The target 38 also includes an impact block 37 positioned adjacent the target support 39 to intercept the projectile 16 in its trajectory. The impact block 37 is preferably formed from a yielding, deformable material, such as wood, to dissipate the force of impact. If desired, the size, orientation and other characteristics of the impact block 37 can be selected so that the depth of penetration of the projectile 16 into the impact block 37 can be correlated with the force of impact, projectile velocity, projectile orientation, or other characteristics of the projectile 16 and its trajectory.

A slidable hood 130 formed from a translucent, shatter resistant material, such as polyethylene, extends between the front end of the barrel 20 and the target 38. The hood 130 shields the impact area on the target 38 and protects the operator from fragments of the projectile 16 propelled by the force of impact. As best seen in FIG. 4, the hood 130 has an inverted "U" shape and is slidingly affixed to the base 12 by generally "L"-shaped guides 132 positioned in slots formed in the sides of the hood 130. The hood 130 thus may be slid on the guides 32 back from the target 38 to expose the results of an impact test for inspection and to reload the impact test apparatus 10.

A photoelectric system 134 is positioned in apertures in either side of the hood 130 and located in the plane of the trajectory of the projectile 16. The photoelectric system 134 generates electrical signals when the projectile 16 passes the photoelectric system 134 in its trajectory, thus permitting the muzzle velocity of the projectile 16 to be calculated electronically by standard calculating means (not shown).

The trigger means 68 retains the shuttle 40 in a predetermined fixed position in the barrel 20 while the sealed portion of the barrel 20 is pressurized with a compressed gas through the compressed gas supply means 14 (FIG. 1). The trigger means 68 also permits the shuttle 40 to be precisely and reproducibly released after a predetermined pressure has been achieved within the barrel 20. The enlarged sectional views of FIGS. 6 and 7 respectively show the shuttle 40 immediately prior and subsequent to release.

As best seen in FIGS. 6 and 7, the trigger means 68 includes a first or female latch member 54 secured within a threaded, axial rear bore 52 positioned in the rear section 44 of the shuttle 40. The female latch member 54 preferably has a generally cylindrical axial latch bore 58 and a square exterior thread 56 adapted to securely engage a square interior thread formed on the surface of the rear bore 52 to affix the female latch member 54 to the shuttle 40. The female latch member 54 also has a first generally circular annular groove or latch groove 60 formed in the cylindrical interior surface of the latch bore 58 for a purpose described below.

The trigger means 68 also includes a second or male latch member 70 (FIGS. 3, 6 and 7) adapted to engage the female latch member 54 to retain the shuttle 40 against an exterior force tending to displace the shuttle 40 and the male latch member 70 relative to one another, such as the force exerted by compressed gas in the sealed portion of the barrel 20. The male latch member 70 includes an elongated generally cylindrical tubular member 72 having a plurality of generally annular, spaced stop grooves 92 formed in the exterior surface of the tubular member 72 (FIG. 3) for a purpose described below. The male latch member 70 also includes an elongated generally cylindrical actuator member or actuator 76 (best seen in FIG. 6) adapted for sliding displacement within the tubular member 72 and positioned in the tubular member 72 proximate the front end thereof.

The actuator 76 has a generally cylindrical front portion. A second generally circular annular groove or actuator groove 78 is formed in the exterior cylindrical surface of the front portion of the actuator 76. The actuator 76 has a recess 80 formed proximate the rear of the actuator 76. The recess 80 has a generally flat surface 81 formed parallel to the axis of the actuator 76. The portion of the actuator 76 to the rear of the recess 80 is flattened in a plane parallel to the flat surface of the recess 80 to form a tab 82. The axial length of the tab 82 is less than the axial length of the flat surface 81 of the recess 80.

The trigger means 68 further includes an elongated trigger rod 84, best seen in FIGS. 3, 6 and 7, extending within the tubular member 72. The front end of the trigger rod 84 has a recess 88 and tab 86 formed therein in the same manner as the recess 80 and tab 82 formed in the actuator 76. The tab 86 of the trigger rod 84 is positioned in the recess 80 in the actuator 76 and the tab 82 of the actuator 76 is positioned in the recess 88 in the trigger rod 84, as best seen in FIG. 6. The tabs 82, 86 and recesses 80, 88 are adapted to permit the tabs 82, 86 to freely slide within the recesses 88, 80 when the trigger rod 84 is moved relative to the actuator 76 over a predetermined axial distance. However, for example, rearward movement of the trigger rod 84 relative to the actuator 76 will ultimately cause the tab 86 formed in the trigger rod 84 to engage the tab 82 formed in the actuator 76, and further rearward motion of the trigger rod 84 will cause the actuator 76 to also travel rearward as the actuator 76 is pulled by the trigger rod 84.

The tubular member 72 has a plurality of generally circular openings 74 formed in the tubular member 72 proximate the front end thereof and centered on a circle around the tubular member 72. As best seen in FIGS. 6 and 7, the openings 74 have a generally trapezoidal vertical cross section with a larger diameter on the interior surface of the tubular member 72 than on the exterior surface of the tubular member 72. The male latch member 70 further includes a plurality of balls 90 with one ball positioned in each opening 74. The balls 90 have a diameter which is selected to allow the balls 90 to protrude through the larger diameter of openings 74 formed in the tubular member 72, but which is less than the smaller diameter of the openings 74 so the balls 90 cannot pass completely through the openings 74.

The position of the balls 90 in the openings 74 depends on whether the actuator groove 78 is aligned with the openings 74. When the actuator groove 78 is aligned with the openings 74, as in FIG. 7, the balls 90 can be seated in the actuator groove 78 which is adapted to receive the balls 90. In this case the balls 90 do not protrude beyond the walls of the tubular member 72. Thus, the shuttle 40 is released.

Alternatively, as shown in FIG. 6, when the actuator groove 78 is not aligned with the openings 74 the balls 90 are seated in the openings 74. In this case, the balls 90 contact the generally cylindrical exterior surface of the front portion of the actuator 76 and protrude through the openings 74 beyond the exterior surface of the tubular member 72 into the latch groove 60. This locks the male latch member 70 to the female latch member 54.

The latch groove 60 is formed with at least one camming surface adapted to impart a normal force to the balls 90 when force is applied to withdraw the male latch member 70 from the female latch member 54. Unless the actuator groove 78 is aligned with the openings 74, the balls 90 cannot move and the male and female latch members 70, 54 remain locked together.

Although a particular presently preferred embodiment of a trigger latch release structure has been illustrated and described, any other different type of instantaneous release system could be used so long as reproducible results could be achieved with it.

The rear end member 26 has a generally cylindrical bore formed therein and positioned to be centered axially with respect to the barrel 20, as shown in FIG. 3. The bore in the rear end member 26 is adapted to securely receive a generally tubular collet 100 having fingers and a lock ring which are adapted to support the tubular member 72 and to securely engage the stop grooves 92 formed on the exterior surface of the tubular member 72 in a conventional manner. The collet 100 has a generally cylindrical axial bore in which is formed a generally annular circular groove to securely retain a seal 102. The seal 102 is a generally ring-shaped seal preferably formed from an elastomeric material, such as an O-ring, and is adapted to sealingly engage the exterior surface of the tubular member 72 thus sealing compressed gas within the barrel 20. The collet 100 can be loosened and the tubular member 72 can be displaced inwardly or outwardly with respect to the barrel 20 as desired to vary the distance which the shuttle 40 travels within the barrel 20 when the shuttle 40 is released. This permits the muzzle velocity of the projectile 16 to be varied and permits the shuttle 40 to be loaded with projectiles 16 of various sizes.

The trigger rod 84 terminates proximate the rear end of the tubular member 72 which is closed with a threaded cap 106 as best seen in FIG. 3. A trigger 110, which functions to release the shuttle 40, includes a biasing means or spring 108 which extends between the rear end of the trigger rod 84 and the cap 106 to bias the trigger rod 84 forward. The trigger 110 further includes a trigger block 112, having a generally cylindrical bore formed therein to receive the tubular member 72, and a handle 120. The trigger block 112 is securely affixed to the tubular member 72 by set screws (FIG. 3) proximate the rear end of the tubular member 72. The trigger block 112 has a first generally cylindrical hole formed therein perpendicular to the longitudinal axis of the tubular member 72. A first pin 114 is located in the first hole and pivotably secures the handle 120 to the trigger block 112.

A second pin 116 extends through a second hole formed in the trigger rod 84 proximate the rear end of the trigger rod 84 and perpendicular to the longitudinal axis of the trigger rod 84. The second pin 116 extends outwardly through a pair of arcuate slots 118 formed in the tubular member 72 and is securely held by the handle 120, as best seen in FIGS. 3 and 5.

In operation, the operator grasps the handle 120 at the rear end of the tubular member 72 and squeezes the handle 120 toward the tubular member 72. As the handle 120 pivots on the first pin 114 the second pin 116 extending through the trigger rod 84 forces the trigger rod 84 back against the spring 108. At a predetermined point, the trigger rod 84 engages the actuator 76 and draws the actuator 76 back within the tubular member 72. When the actuator groove 78 aligns with the openings 74 the balls 90 are forced by the camming surface of the latch groove 60 through the openings 74 into the actuator groove 78 and the shuttle 40 is free to travel forward. When the handle 120 is released the spring 108 forces the trigger rod 84 and actuator 76 forward. A camming surface on the actuator groove 78 forces the balls 90 into the openings 74 in the tubular member 72.

To reload the impact test apparatus 10 the pressure within the barrel 20 is released through the valve 15 and the shuttle 40 is reloaded with a projectile 16 placed in the sample chamber 46. The loaded shuttle 40 is forced backward within the barrel 20 manually with an elongated member such as a rod or tube (not illustrated) until the shuttle 40 engages the front end of the tubular member 72. The handle 120 is then squeezed to draw back the actuator 76 and to align the actuator groove 78 with the openings 74 to permit the male latch member 70 to be inserted into the female latch member 54. The handle 120 is then released and the shuttle 40 is pushed back onto the tubular member 72 until the openings 74 in the tubular member 72 confront the latch groove 60. The force of the spring 108 acting through the camming surface of the actuator groove 78 forces the balls 90 radially outwardly up through the openings 74 to extend into the latch groove 60. At the same time, the actuator 76 is forced forward by the spring 108, thereby displacing the actuator groove 78 forward with respect to the openings 74, and thus securely latching the male latch member 70 to the female latch member 54.

The impact test apparatus of present invention advantageously requires a relatively small amount of laboratory floor space. High muzzle velocities may be obtained without the use of a tower which is expensive to construct and which requires substantial space. Further, the use of hazardous explosive charges is avoided. Because the projectile need travel only a short distance after leaving the shuttle 40 before impacting on the target 38, the orientation of the projectile 16 relative to the target 38 is affected less by the aerodynamic characteristics of the projectile 16 than in the case in which the projectile 16 is dropped from a high tower. Thus, the operator has greater ability to control the variables relating to the projectile 16 impacting on the target 38.

From the foregoing description, it can be seen that the present invention comprises an impact test apparatus 10 for conveniently and reproducibly testing the effect of impact on projectiles and their components. It will be recognized by those skilled in the art that changes may be made to the above-described embodiment of the invention without departing from the broad inventive concepts thereof. For example, the barrel 20 may be formed from tubular stock having a noncircular cross section such as a square or rectangular cross section, provided that the cross section of the shuttle 40 is modified as appropriate to maintain the seal between the shuttle 40 and the barrel 20. Similarly, the target 38 may be removed from the base 12 and the trajectory of the projectile 16 launched by the impact test apparatus 10 may be studied. Different triggering mechanisms can also be used, so long as they provide for instantaneous, reproducible release of the shuttle. It is understood, therefore, that this invention is not limited to the particular embodiment disclosed, but is intended to cover modifications which are within the scope and spirit of the invention as defined by the appended claims.

I claim:

1. An impact test apparatus comprising:

a barrel adapted to contain pressurized gas and having a sealed end and an opposed open end;

a shuttle positioned for translation within the barrel, the shuttle including means for releasably carrying a test sample and sealing means for sealingly engaging the barrel, the sealing means dividing the interior of the barrel into a portion open to the atmosphere and a sealed portion;

means for supplying pressurized gas to the sealed portion of the interior of the barrel;

trigger means for selectively retaining the shuttle in a fixed position in the barrel and for releasing the shuttle to permit the shuttle to accelerate toward the open end of the barrel as the pressurized gas in the sealed portion of the barrel expands; and stopping means proximate the open end of the barrel to decelerate the shuttle and retain the shuttle substantially within the barrel while allowing the test sample to travel toward a target aligned with the open end of the barrel.

2. A test apparatus according to claim 1 wherein the stopping means comprises at least one brake ring having an exterior surface formed to abut the interior of the barrel and an axially centered opening formed therein, the interior of the opening being adapted to engage the shuttle, the brake ring being formed from a resilient material, and ring retention means for retaining the brake ring in the barrel when the brake ring is engaged by the shuttle.

3. A test apparatus according to claim 2 wherein the brake ring has a generally cylindrical exterior surface, and a generally cylindrical opening, the interior diameter of the opening being slightly smaller than the exterior diameter of the front section of the shuttle.

4. A test apparatus according to claim 3 wherein the ring retention means includes a retention member having an axially centered, generally cylindrical aperture with a diameter approximately the same as the diameter of the opening in the brake ring, the retention member being affixed to the open end of the barrel proximate the brake ring.

5. A test apparatus according to claim 1 wherein the barrel and shuttle are generally cylindrical, the shuttle including a front section having a front end and adapted to engage the stopping means, and a rear section adapted to engage the trigger means.

6. A test apparatus according to claim 5 wherein the shuttle contains an axially centered, generally cylindrical bore for receiving and carrying the test sample.

7. A test apparatus according to claim 6 wherein the front and rear sections of the shuttle are generally cylindrical and have the same axis of radial symmetry, the diameter of the rear section being slightly less than the interior diameter of the barrel, the diameter of the front section being less than the diameter of the rear section, a generally annular shoulder being formed between the front and rear sections, the outside edge of the front end of the shuttle being chamfered.

8. A test apparatus according to claim 6 wherein the trigger means includes:

a tubular member having a front and a back end, the tubular member being adjustably affixed to the barrel proximate the closed end, the tubular member extending through the closed end in sealing engagement with the closed end; and latching means for securing the shuttle to the trigger means proximate the front end of the tubular member, the latching means including actuation means for releasing the shuttle.

9. A test apparatus according to claim 8 wherein the actuation means includes a trigger rod positioned inside the tubular member and extending from proximate the back end of the tubular member to proximate the latching means, the shuttle being released by displacement of the trigger rod within the tubular member.

10. A test apparatus according to claim 9 wherein the actuation means further includes biasing means for biasing the trigger rod away from the back end of the tubular member, the shuttle being released by rearward displacement of the trigger rod.

11. A test apparatus according to claim 10 wherein the trigger member further includes lever means pivotably mounted on the tubular member for displacing the trigger rod within the tubular member.

12. A test apparatus according to claim 8 wherein the shuttle includes a threaded axial bore in the rear section of the shuttle for receiving a generally cylindrical latch engaging means having an exterior thread adapted to engage the interior thread of the axial bore.

13. A test apparatus according to claim 12 wherein the threads of the axial bore of the rear section of the shuttle and the exterior threads of the latch engaging means having generally square cross sections.

14. A test apparatus according to claim 13 wherein the latch engaging means has an axially centered opening for receiving the front end of the tubular member.

15. A test apparatus according to claim 1 additionally comprising means for measuring the velocity of the test sample as it exits the open end of the barrel.

16. A test apparatus according to claim 1 additionally comprising target means for terminating the trajectory of the test sample.

* * * * *